US006980974B2

(12) United States Patent
Kobayashi et al.

(10) Patent No.: US 6,980,974 B2
(45) Date of Patent: Dec. 27, 2005

(54) METHOD FOR PROCESSING EXPRESSION DATA OF GENES

(75) Inventors: Takeshi Kobayashi, Nagoya (JP); Hiroyuki Honda, Nagoya (JP); Taizo Hanai, Fukuoka (JP); Tatsuya Ando, Nagoya (JP)

(73) Assignee: Nagoya Industrial Science Research Institute, Nagoya (JP)

( * ) Notice: Subject to any disclaimer, the term of this patent is extended or adjusted under 35 U.S.C. 154(b) by 173 days.

(21) Appl. No.: 10/321,633

(22) Filed: Dec. 18, 2002

(65) Prior Publication Data

US 2003/0233196 A1    Dec. 18, 2003

(30) Foreign Application Priority Data

Jun. 17, 2002 (JP) .............................. 2002-175631
Oct. 16, 2002 (JP) .............................. 2002-301695

(51) Int. Cl.[7] ..................... G01N 33/48; G06G 7/48; G06F 15/18; G06E 1/00; G06E 3/00
(52) U.S. Cl. ..................... 706/21; 702/19; 702/20; 703/11; 706/2; 706/13; 706/924
(58) Field of Search ..................... 702/19, 20; 703/11; 706/2, 13, 21; 435/6; 536/23.1

(56) References Cited

OTHER PUBLICATIONS

Ando et al. Genome Informatics, vol. 12: 247-248, 2001.*
Listing of papers presented in Genome Informatics vol. 12, 2001, which are also presented at the 12th International Conferenc on Genome Informatics held Dec. 17-19, 2001 in Japan. Printed on Dec. 9, 2004 from website http://www.jsbi.org/journal/GI12.html.*
Ando et al., Jpn. J. Cancer Res., vol. 93, pp. 1207-1212, Nov., 2002.*

* cited by examiner

*Primary Examiner*—John Brusca
*Assistant Examiner*—Shubo (Joe) Zhou
(74) *Attorney, Agent, or Firm*—Westerman, Hattori, Daniels & Adrian, LLP

(57) ABSTRACT

The expression data of specimen genes are processed using the SWEEP operator method and the parameter increasing method, and genes are selected. A FNN model is constructed by making the expression data of the selected genes as input variables.

11 Claims, 16 Drawing Sheets

SWEEP operator method

Regression equations without any constant term are capable of being expressed as follows:

$$\begin{cases} a_1 wfa + b_1 wfb + c_1 wfc + d_1 wfd = y_1 \\ a_2 wfa + b_2 wfb + c_2 wfc + d_2 wfd = y_2 \\ a_3 wfa + b_3 wfb + c_3 wfc + d_3 wfd = y_3 \\ \vdots \end{cases}$$

FIG.2

Order of genes when the prognosis prediction was performed with one input.

| Order | Genes | Accession No. |
|---|---|---|
| ① | KIAA0278 gene, partial cds. | D87468_at |
| 2 | BAC clone GS244B22 from 7q21-q22, complete sequence | AC002450_at |
| ③ | TRANSDUCIN-LIKE ENHANCER PROTEIN 1 | M99435_at |
| ④ | HADHA Hydroxyacyl-Coenzyme A dehydrogenase | D16480_at |
| 5 | Splicing factor SF3a120 | X85237_at |
| ⑥ | Oviductal glycoprotein mRNA | U09550_at |
| 7 | PTGER2 Prostaglandin E receptor 2 (subtype EP2), 53kD | L28175_at |
| ⑧ | Nuclear antigen H731 mRNA | U83908_at |
| 9 | Splicing factor SRp55-2 (SRp55) mRNA | U30828_at |
| 10 | S-ARRESTIN | X12453_at |
| 11 | TOP1 DNA topoisomerase 1 | U07804_s_at |
| 12 | Axonemal dynein heavy chain (partial, ID hdhc3) | Z83802_at |
| ⑬ | Msg1-related gene 1 (mrg1) mRNA | U65093_at |
| 14 | Butyrophilin (BT3.3) gene | U97502_rna1_at |
| 15 | Nadh-Ubiquinone Oxidoreductase, 51 Kda Subunit | HG4747-HT5195_at |
| 16 | 26 S protease subunit 5b | S79862_s_at |
| 17 | PAX3 Paired box homeotic gene 3 | S69369_at |
| 18 | TYROSINE-PROTEIN KINASE RECEPTOR ECK PRECURSOR | M59371_at |
| 19 | LCN1 Lipocalin 1 | L14927_at |
| 20 | Pre-pro-megakaryocyte potentiating factor | U40434_at |
| 21 | ADRB3 Adrenergic, beta-3-, receptor | X70811_at |
| 22 | Karyopherin alhph 3 | Y12394_at |
| 23 | CTSE Cathepsin E | J05036_s_at |
| 24 | Hyaluronan synthase 3 (HAS3) gene, partial cds | U86409_at |
| 25 | VEGF Vascular endothelial growth factor | M27281_at |
| 26 | PERIPHERIN | L14565_at |
| 27 | SM15 gene (human interferon-related protein SM15 (U09585) | U73167_cds5_at |
| 28 | PEPTIDYL-PROLYL CIS-TRANS ISOMERASE | M80254_at |
| 29 | Guanine Nucleotide-Binding Protein Hsr1 | HG3227-HT3404_at |
| 30 | Zinc finger protein mRNA | U68536_at |

Table 1 Order of genes

○ contained in 100 pieces of genes which have been sequenced by Shipp et al.

◎ genes which have been used for the prognosis prediction by Shipp et al.

Combination selected when one gene was fixed
1: KIAA0278 gene

FIG.3

| | Selected Genes | Accession No. |
|---|---|---|
| ① | KIAA0278 gene, partial cds | D87468_at |
| ② | Nuclear antigen H731 mRNA | U83908_at |
| 3 | HIV-1 Nef interacting protein (Nip7-1) | U83843_at |
| 4 | CRTM Cartilage matrix protein | M65682_s_at |
| 5 | Apolipoprotein A-I | X04898_rna1_at |
| 6 | ZNF44 Zinc finger protein 44 (KOX 7) | X16281_at |

2: BAC clone GS244B22 from 7q21-q22

| | Selected Genes | Accession No. |
|---|---|---|
| 1 | BAC clone GS244B22 from 7q21-q22 | AC002450_at |
| 2 | SNCB Synuclein, beta | S69965_at |
| 3 | Interferon-gamma induced protein (IFI 16) gene | M63838_s_at |
| 4 | SLO Homolog of Drosophila slowpoke | U11717_s_at |
| 5 | Putative cyclin G1 interacting protein | U61836_at |
| 6 | FOLATE RECEPTOR BETA PRECURSOR | J02876_at |

3: TRANSDUCIN-LIKE ENHANCER PROTEIN 1

| | Selected Genes | Accession No. |
|---|---|---|
| ① | TRANSDUCIN-LIKE ENHANCER PROTEIN 1 | M99435 |
| ② | Oviductal glycoprotein mRNA | U09550 |
| ③ | CDKN2A Cyclin-dependent kinase inhibitor 2A (melanoma, p16, inhibits CDK4) | U26727 |
| 4 | Receptor tyrosine kinase DDR gene | U48705 |
| 5 | VIL2 Villin 2 (ezrin) | X51521 |
| 6 | IGF1R Insulin-like growth factor 1 receptor | X04434 |

4: HADHA Hydroxyacyl-Coenzyme A dehydrogenase

| | Selected Genes | Accession No. |
|---|---|---|
| ① | HADHA Hydroxyacyl-Coenzyme A dehydrogenase | D16480_at |
| ② | Cytoplasmic antiproteinase 2 (CAP2) mRNA | L40377_at |
| 3 | ADRB3 Adrenergic, beta-3-, receptor | X70811_at |
| 4 | PRKACB gene (protein kinase C-beta-2) | M18255_cds2_s_at |
| 5 | NF-AT3 mRNA | L41066_at |
| 6 | Death domain receptor 3 soluble form (DDR3) mRNA | U83598_at |

5: Splicing factor SF3a120

| | Selected Genes | Accession No. |
|---|---|---|
| 1 | Splicing factor SF3a120 | X85237_at |
| 2 | RNA-BINDING PROTEIN FUS/TLS | U00928_at |
| 3 | SPIB Spi-B transcription factor (Spi-1/PU.1 related) | X66079_at |
| 4 | Axonemal dynein heavy chain (partial, ID hdhc3) | Z83802_at |
| 5 | S-ARRESTIN | X12453_at |
| 6 | Chromosomal-Translocation Associated Gene Ltg19/Enl | HG3362-HT3539_s_at |

○ contained in 100 pieces of genes which have been sequenced by Shipp et al.

◎ genes which have been used for the prognosis prediction by Shipp et al.

Fuzzy rules of Example 1

TRANSDUCIN-LIKE ENHANCER PROTEIN 1/4 INPUT

FIG.5(A)

| | | | | TRANSDUCIN-LIKE ENHANCER PROTEIN 1 | | | |
|---|---|---|---|---|---|---|---|
| | | | | S | | B | |
| | | | | Oviductal glycoprotein mRNA | | | |
| | | | | S | B | S | B |
| CDKN2A Cyclin-dependent kinase inhibitor 2A (melanoma, p16, inhibits CDK4) | S | Receptor tyrosine kinase DDR gene | S | -3.02 | 0.01 | 0.86 | 0.65 |
| | | | B | 3.81 | 2.75 | 1.25 | 1.11 |
| | B | | S | 4.94 | 2.37 | 0.96 | 0.59 |
| | | | B | -7.22 | -1.79 | 0.88 | 1.12 |

FIG.5(B)

| | | | | TRANSDUCIN-LIKE ENHANCER PROTEIN 1 | | | |
|---|---|---|---|---|---|---|---|
| | | | | S | | B | |
| | | | | Oviductal glycoprotein mRNA | | | |
| | | | | S | B | S | B |
| CDKN2A Cyclin-dependent kinase inhibitor 2A (melanoma, p16, inhibits CDK4) | S | Receptor tyrosine kinase DDR gene | S | * | 36,40,50, 57,58 | 34,35,47, 48,54 | 41 |
| | | | B | 2, 10, 37, 44, 45 | | 13, 33 | |
| | B | | S | 3, 39, 46, 51, ㊵, ㊻ | 38, 49, 55 | 42 | |
| | | | B | | 17 | 52 | |

* 1, 4, 5, 6, 7, 8, 9, 11, 12, 14, 15, 16, 18~32, ㊸

In the case where the expression data of TRANSDUCIN is small, the expression data of CDKN2A is large, and the expression data of Receptor tyrosine kinase is small, the prognosis is poor.

Fuzzy rules of Example 2
TRANSDUCIN-LIKE ENHANCER PROTEIN 1/5 INPUT

FIG.6(A)

| CDKN2A Cyclin-dependent kinase inhibitor 2A (melanoma, p16, inhibits CDK4) | Receptor tyrosine kinase DDR gene | VIL2 Villin 2 (ezrin) | | TRANSDUCIN-LIKE ENHANCER | | | |
|---|---|---|---|---|---|---|---|
| | | | | S | | B | |
| | | | | Oviductal glycoprotein mRNA | | | |
| | | | | S | B | S | B |
| S | S | S | S | -2.13 | 0.38 | 1.01 | 0.98 |
| S | S | S | B | -3.00 | 1.29 | 0.07 | 1.03 |
| S | S | B | S | 2.41 | 1.89 | 1.21 | 1.02 |
| S | S | B | B | 3.12 | 2.33 | 2.15 | 1.25 |
| S | B | S | S | 3.64 | 1.82 | 1.45 | 0.68 |
| S | B | S | B | 3.27 | 2.25 | 1.46 | 1.02 |
| S | B | B | S | -3.01 | -0.45 | -1.62 | 0.12 |
| S | B | B | B | -6.03 | -1.97 | 0.20 | 0.49 |

FIG.6(B)

| CDKN2A Cyclin-dependent kinase inhibitor 2A (melanoma, p16, inhibits CDK4) | Receptor tyrosine kinase DDR gene | VIL2 Villin 2 (ezrin) | | TRANSDUCIN-LIKE ENHANCER PROTEIN 1 | | | |
|---|---|---|---|---|---|---|---|
| | | | | S | | B | |
| | | | | Oviductal glycoprotein mRNA | | | |
| | | | | S | B | S | B |
| S | S | S | S | * | 36, 40, 41, 57, 58 | 35 | |
| S | S | S | B | * * | 50 | 34, 47, 48, 54 | |
| S | S | B | S | 2 | | | |
| S | S | B | B | 10, 37, 44 | | 13, ㉝ | |
| S | B | S | S | 27, 51, ㊾ ㊻ | | 42 | |
| S | B | S | B | 3, 39, 46 | 38, 49, 55 | | |
| S | B | B | S | | | | 17 |
| S | B | B | B | | | 52 | |

* 8, 14, 15, 18, 20, 21, 23, 25, 26, 28, 30, 32, 45
* * 1, 4, 5, 6, 7, 9, 11, 12, 16, 19, 22, 24, 29, 31, ㊸

In the case where the expression data of TRANSDUCIN is small,
the expression data of CDKN2A is large, and the expression data
of Receptor tyrosine kinase is small, the prognosis is poor.

Fuzzy rules of Example 3
HADHA/5 input

FIG.7(A)

| ADRB3 Adrenergic, beta-3-, receptor | PRKACB gene (protein kinase C-beta-2) | NF-AT3 mRNA | | HADHA Hydroxyacyl-Coenzyme A | | | |
|---|---|---|---|---|---|---|---|
| | | | | S | | B | |
| | | | | Cytoplasmic antiproteinase 2 (CAP2) | | | |
| | | | | S | B | S | B |
| S | S | | S | 1.13 | 1.51 | 1.78 | -0.40 |
| S | S | | B | -1.44 | 1.49 | 1.49 | 0.62 |
| S | B | | S | 0.48 | -2.61 | 1.07 | 0.49 |
| S | B | | B | 2.93 | -1.48 | -0.57 | -1.00 |
| B | S | | S | -1.27 | -1.19 | 0.19 | 0.05 |
| B | S | | B | 1.53 | -0.54 | -0.78 | -0.53 |
| B | B | | S | 2.01 | 2.52 | 1.06 | 1.28 |
| B | B | | B | -2.35 | 0.25 | -2.69 | -0.74 |

FIG.7(B)

| ADRB3 Adrenergic, beta-3-, receptor | PRKACB gene (protein kinase C-beta-2) | NF-AT3 mRNA | | HADHA Hydroxyacyl-Coenzyme A dehydrogenase | | | |
|---|---|---|---|---|---|---|---|
| | | | | S | | B | |
| | | | | Cytoplasmic antiproteinase 2 (CAP2) mRNA | | | |
| | | | | S | B | S | B |
| S | S | | S | 29, 43, 56, 57 | 1, 7, 12, ㊹ | 37, 38, 53 | 3, 13, 23 |
| S | S | | B | 24, 26, 27, 30 | 6, 9, ㊽ | 16, 31, 45, ㊾, 50 | 17 |
| S | B | | S | 47 | 19 | 34, 42, 46, 51 | |
| S | B | | B | 40, 54 | 25 | | |
| B | S | | S | 2, 4, 21 | 5, 8, 18 | | 22 |
| B | S | | B | 15, 20, 32, ㉟ | 10, 11 | | |
| B | B | | S | 39 | | ㉘, 33, 36, 41, 48, 52, 55 | |
| B | B | | B | 14 | | | |

- In the case where the expression data of HADHA is large, the expression data of CAP2 is small and the expression data of NF-AT3 is small, the prognosis is poor.
- In the case where the expression data of ADRB3 is large, the expression data of PKACB is large, and the expression data of NF-AT3 is small, the prognosis is poor.

CONVENTIONAL METHOD

FNN model of example 1

FIG.9

Upper order 10 genes selected using SWEEP operator method

| Order | Selected Genes | Accession No. |
|---|---|---|
| 1 | Homo sapiens CEGP1 protein (CEGP1), mRNA. | NM_020974 |
| 2 | NY-REN-24 antigen | AF052087 |
| 3 | ESTs | |
| 4 | phosphatidylinositol (4, 5) bisphosphate 5-phosphatase, A | U45975 |
| 5 | Homo sapiens cDNA FLJ13591 fis, clone PLACE1009410 | AL049689 |
| 6 | hypothetical protein similar to tenascin-R | AF148505 |
| 7 | methylmalonate-semialdehyde dehydrogenase | NM_005744 |
| 8 | ariadne (Drosophila) homolog, ubiquitin-conjugating enzyme E2-binding protein | AL080059 |
| 9 | Homo sapiens mRNA; cDNA DKFZp564H142 (from clone DKFZp564H142) | |
| 10 | HSPC150 protein similar to ubiquitin-conjugating enzyme | NM_014176 |

Selected genes (gene which has been first inputted was fixed)

FIG.10

1. Homo sapiens CEGP1 protein (CEGP1), mRNA.

|   | Selected Genes | Accession No. |
|---|---|---|
| 1 | Homo sapiens CEGP1 protein (CEGP1), mRNA | NM_020974 |
| 2 | ADP-ribosylation factor 4-like | NM_001661 |
| 3 | DNA segment on chromosome X (unique) 9879 expressed sequence | NM_006014 |
| 4 | UDP-glucose glycoprotein glucosyltransferase 1 | |
| 5 | Homo sapiens mRNA full length insert cDNA clone EUROIMAGE 137356 | AL109679 |
| 6 | ESTs | |

2. NY-REN-24 antigen

|   | Selected Genes | Accession No. |
|---|---|---|
| 1 | NY-REN-24 antigen | AF052087 |
| 2 | Homo sapiens mRNA; cDNA DKFZp564H142 (from clone DKFZp564H142) | AL080059 |
| 3 | carbonic anhydrase IX | NM_001216 |
| 4 | myosin, light polypeptide, regulatory, non-sarcomeric (20kD) | NM_006471 |
| 5 | solute carrier family 26, member 3 | NM_000111 |
| 6 | ESTs | |

3. ESTs

|   | Selected Genes | Accession No. |
|---|---|---|
| 1 | ESTs | |
| 2 | ESTs, Weakly similar to unnamed protein product [H.sapiens] | |
| 3 | chromosome 21 open reading frame 22 | |
| 4 | postmeiotic segregation increased 2-like 8 | NM_005394 |
| 5 | DNA segment on chromosome X and Y (unique) 155 expressed sequence | L03426 |
| 6 | signal recognition particle 54kD | NM_003136 |

4. phosphatidylinositol (4,5) bisphosphate 5-phosphatase, A

|   | Selected Genes | Accession No. |
|---|---|---|
| 1 | phosphatidylinositol (4,5) bisphosphate 5-phosphatase, A | U45975 |
| 2 | PCTAIRE protein kinase 3 | AL161977 |
| 3 | heat shock protein, DNAJ-like 2 | NM_001539 |
| 4 | ESTs | |
| 5 | ESTs, Weakly similar to unnamed protein product [H.sapiens] | |
| 6 | ESTs | |

5. Homo sapiens cDNA FLJ13591 fis, clone PLACE1009410

|   | Selected Genes | Accession No. |
|---|---|---|
| 1 | Homo sapiens cDNA FLJ13591 fis, clone PLACE1009410 | |
| 2 | Homo sapiens PAC clone RP1-130H16 from 22q12.1-qter | |
| 3 | serine (or cysteine) proteinase inhibitor, clade B (ovalbumin), member 1 | M93056 |
| 4 | DNA polymerase epsilon p12 subunit | NM_019896 |
| 5 | ubiquitin-conjugating enzyme E2N (homologous to yeast UBC13) | NM_003348 |
| 6 | AFG3 (ATPase family gene 3, yeast)-like 2 | NM_006796 |

FIG.11

6. hypothetical protein similar to tenascin-R

| | Selected Genes | Accession No. |
|---|---|---|
| 1 | hypothetical protein similar to tenascin-R | AL049689 |
| 2 | beclin 1 (coiled-coil, myosin-like BCL2-interacting protein) | NM_003766 |
| 3 | HSPC065 protein | NM_014157 |
| 4 | Homo sapiens cDNA: FLJ23228 fis, clone CAE06654 | Contig49670_R |
| 5 | KIAA1094 protein | NM_014908 |
| 6 | ESTs | |

7. methylmalonate-semialdehyde dehydrogenase

| | Selected Genes | Accession No. |
|---|---|---|
| 1 | methylmalonate-semialdehyde dehydrogenase | AF148505 |
| 2 | p30 DBC protein | AL137523 |
| 3 | ESTs | |
| 4 | lysophosphatidic acid acyltransferase-gamma1 | NM_020132 |
| 5 | clathrin, light polypeptide (Lcb) | NM_001834 |
| 6 | NY-REN-45 antigen | NM_016121 |

8. ariadne (Drosophilia)homolog, ubiquitin-conjugating enzyme E2-binding protein, 1.

| | Selected Genes | Accession No. |
|---|---|---|
| 1 | ariadne (Drosophila) homolog, ubiquitin-conjugating enzyme E2-binding pro | NM_005744 |
| 2 | transforming growth factor, beta 3 | NM_003239 |
| 3 | Homo sapiens cDNA FLJ11354 fis, clone HEMBA1000129, weakly similar to HYPOTHETICAL HELICASE C8A4.08C in CHROMOSOME I | |
| 4 | nudix (nucleoside diphosphate linked moiety X)-type motif 1 | NM_002452 |
| 5 | preferentially expressed antigen in melanoma | NM_006115 |
| 6 | ESTs | |

9. Homo sapiens mRNA; cDNA DKFZp564H142 (from clone DKFZp564H142)

| | Selected Genes | Accession No. |
|---|---|---|
| 1 | Homo sapiens mRNA; cDNA DKFZp564H142 (from clone DKFZp564H142) | AL080059 |
| 2 | NY-REN-24 antigen | AF052087 |
| 3 | carbonic anhydrase IX | NM_001216 |
| 4 | myosin, light polypeptide, regulatory, non-sarcomeric (20kD) | NM_006471 |
| 5 | solute carrier family 26, member 3 | NM_000111 |
| 6 | ESTs | |

10. HSPC150 protein similar to ubiquitin-conjugating enzyme

| | Selected Genes | Accession No. |
|---|---|---|
| 1 | HSPC150 protein similar to ubiquitin-conjugating enzyme | NM_014176 |
| 2 | ubiquitin C | M26880 |
| 3 | UDP-glucose:glycoprotein glucosyltransferase 1 | |
| 4 | ESTs, Weakly similar to KIAA1435 protein [H.sapiens] | |
| 5 | KIAA1557 protein | |
| 6 | proteasome (prosome, macropain) subunit, alpha type, 4 | NM_002789 |

: genes selected twice
No.2 and No.9 are different in selected order, but completely the same gene was selected.

FIG. 14

Fuzzy rules (93.8%) of Drosophila homolog, ubiquitin-conjugating-6 inputs

| | | | | | ubiquitin-conjugating enzyme E2-binding protein | | | | | | | |
|---|---|---|---|---|---|---|---|---|---|---|---|---|
| | | | | | S | | | | B | | | |
| | | | | | transforming growth factor, beta 3 | | | | | | | |
| | | | | | S | | B | | S | | B | |
| | | | | | Homo sapiens cDNA | | | | | | | |
| | | | | | S | B | S | B | S | B | S | B |
| nudix-type motif 1 | S | ESTs | S | preferentially expressed antigen in melanoma | S | 0.92 | -0.72 | 2.30 | 0.16 | 1.04 | 1.14 | 0.13 | -0.08 |
| | | | | | B | 0.45 | 1.39 | 0.19 | 0.78 | 0.82 | 0.94 | 1.10 | 1.17 |
| | | | B | | S | -0.62 | 0.38 | -0.48 | -0.15 | -0.70 | 0.45 | 2.10 | 0.47 |
| | | | | | B | -0.27 | 0.07 | 0.05 | -0.09 | 1.40 | -0.39 | 0.82 | -0.30 |
| | B | | S | | S | 4.96 | 0.21 | 1.32 | 0.34 | 0.22 | -1.12 | -0.85 | 0.26 |
| | | | | | B | 0.23 | 0.32 | 0.05 | 0.13 | 1.10 | 0.91 | 0.25 | 0.08 |
| | | | B | | S | 0.36 | 0.07 | 0.20 | 0.46 | 0.64 | -0.41 | -0.29 | -0.07 |
| | | | | | B | 0.05 | 0.03 | 0.01 | 0.02 | 0.91 | 0.64 | 0.22 | 0.07 |

· In the case where the expression data of ubiquitin-conjugating enzyme E2-binding protein is large, the expression data of transforming growth factor, beta-3 is small, the expression data of nudix-type motif 1 is small and the expression data of ESTs is small, the prognosis is poor.

· In the case where the expression data of ubiquitin-conjugating enzyme E2-binding protein is large, the expression data of nudix-type motif 1 is small, the expression data of ESTs is small and the expression data of preferentially expressed antigen in melanoma is large, the prognosis is poor.

  : Combinations of gene expressions whose prognosis is poor

FIG.15

Combinations to which the respective patients are relevant

| (4) nudix-type motif 1 | (6) ESTs | preferentially expressed antigen in melanoma | (5) | (1) ubiquitin-conjugating enzyme E2-binding protein S / (2) transforming growth factor, beta 3 S / (3) Homo sapiens cDNA FLJ11354 fis S | (1) S / (2) S / (3) B | (1) S / (2) B / (3) S | (1) S / (2) B / (3) B | (1) B / (2) S / (3) S | (1) B / (2) S / (3) B | (1) B / (2) B / (3) S | (1) B / (2) B / (3) B |
|---|---|---|---|---|---|---|---|---|---|---|---|
| S | S | S | S | 28, 51 | 2, 25, 32, 118, 58 | (—) | 16, 17, 21, 27, 30, 41, 225, 116, 46 | (—) 69, 70, 73, 75, 78, 79, 107 | 4, 31, 120, 45, 47, 49, 52, 54, 55, 56, 68, 78, 102, 105 | 13, 26, 60, 72 | 1, 3, 5, 6, 7, 9, 10, 11, 14, 18, 19, 22, 23, 39, 40, 43, 115, 117, 61 |
| S | S | B | | | (—) | | | 48, 50, 53, 66, 106 | 57, 59, 63, 64, 65, 67, 103, 104, 108, 109, 110, 111, 112 | (—) | 77, 113 |
| S | B | S | | | 33 | | 29, 36 | 15 | 12, 34 | (—) | 42 |
| S | B | S | | | | | | (—) | 24, 35, 44 | | |
| B | S | S | | | (—) | (—) | | *119*, 62, 71 | 8, 20 | | |
| B | S | B | | | | | | (—) | | | |
| B | B | S | | | 37, 28 | | | | | | |
| B | B | B | | | | | | (dotted) | | | |

Italic type: patient for whom the prediction is incorrect
Light face type: patient whose breast cancer has not metastasized
Bold-faced type: patient whose breast cancer has metastasized

- The combinations of gene expressions which are relevant to the patients whose breast cancer has metastasized and patients whose breast cancer has not metastasized are well consistent with the fuzzy rule.
- In the case where the expression data of ubiquitin-conjugating enzyme E2-binding protein is large, the expression data of transforming growth factor, beta 3 is small, the expression data of nudix type motif 1 is small, and the expression data of ESTs is small, the patients whose prognosis is poor occupy 36/46=78.3% out of the whole metastasized patients.
- In the case where the expression data of ubiquitin-conjugating enzyme E2-binding protein is large, the expression data of nudix-type motif 1 is small, the expression data of ESTs is small, the expression data of preferentially expressed antigen in melanoma is large, the patients whose prognosis is poor occupy 20/46 = 43.5% out of the whole metastasized patients.

METHOD FOR PROCESSING EXPRESSION DATA OF GENES

A compact disk containing a computer program listing has been provided in duplicate (copy 1 and copy 2 of the compact disk are identical). The computer program listing in the compact disk is incorporated by reference herein. The compact disk contains files with their names, size and date of creation as follows: Program list.doc; 112 KB; created Dec. 13, 2002

BACKGROUND OF THE INVENTION

1. Field of the Invention

The present invention relates to a method for processing expression data of two or more genes, and for example, it is preferable method for processing expression data of a large number of genes on a DNA microarray and applying it to the diagnosis.

2. Description of Related Art

In recent years, it has been studied that useful data is extracted from a large quantity of gene expression data obtained from a DNA microarray and it is analyzed. As a general medical statistics analyzing method for this extraction and analyzing method, a logistic regression method or the like is known.

Also by the above-described logistic regression method, gene expression data is capable of being processed and acquiring useful information.

However, in the case where the object of the processing of the gene expression data relates to the diagnosis of the patients, a high reliability is required for the results therefrom. Here, since a logistic regression method is one of linear analysis methods, it is difficult to expect a non-linear phenomenon such as DNA analysis which attempts to find the results by combining the two or more factors with a high precision. Therefore, recently, as a non-linear analyzing method, NN (Neural Network) modeling method has been proposed. The NN modeling method is a modeling method in which learning processes are incorporated, the precision of the expected results is very high. In the diagnosis of the diseases concerned with two or more factors, or the like, the NN method is higher than the logistic regression method in the terms of the expected precision.

On the other hand, in the diagnosis, it is desired to indicate the evidence leading to the diagnosis. As a method capable of deriving such an evidence as well as the results of the diagnosis, the present inventors have directed their attention to the FNN (Fuzzy Neural Network) model which is one of the NN (Neural Network) models.

In order to construct such a FNN model, as similar to the NN model, it is necessary to decide parameters (coefficients) and input variables.

Conventionally, as a method for deciding these parameters and input variables, back propagation method has been proposed. However, it is said that there are 30,000 and over genes of human genome, all these genes are candidates for input variables. It is impossible to make NN of 30,000 pieces of inputs, and it is necessary to select the important genes among them. In a NN method, the smaller the number of input variables is, the easier the input variables are processed, however, there is the limitation which is up to about 20 pieces of input variables. In the case where 30,000 pieces of genes are narrowed down to 20 pieces, the combinations are infinite (about $10^{70}$ ways), the comparisons are not capable of being carried out by determining the parameters in all of the models. Moreover, even in the simple input variable selection method such as parameter increasing method, since the number of the candidates of input items is very large, it requires 100 hours or more even if only one input is selected. If the number of input variables is increased, the calculation time increases in an exponential manner, therefore, if a model with substantially high reliability in which the number of inputs up to around 5 inputs is selected is considered, furthermore, the time of its 50-fold or more is expected to require. Still yet, the number of models constructed by taking such a long time is only one model. It is because the determination of parameters is performed by the back propagation method, and because the time is taken too much to construct one model. As described later, causal relationship between the gene expression and the diagnosis of the onset or prognosis of the diseases is not determined by one pathway, but two or more pathways are involved in. Therefore, in order to expect the causal relationship between the gene expression and the diagnosis of the diseases with a high precision, it is necessary to propose two or more models, the construction of only one model is not sufficient.

SUMMARY OF THE INVENTION

As a result of diligent consideration by taking the above-described matters into account, as a method for deciding the parameters and input variables of a FNN model, a method in which a SWEEP operator method and the parameter increasing method are combined is the most suitable.

First, by the reason described above, in order to select the important genes for the disease from the exhaustive gene expression information of a DNA microarray and construct a model carrying a high reliability for use in the diagnosis, it is not capable of being realized by the combination of the back propagation method and the parameter increasing method. Hence, the combinations of two or more methods have been considered. As a result, as already described above, the method in which the SWEEP operator method and the parameter increasing method are combined is the most suitable for it.

As a method for determining the parameters, the combination of the back propagation (BP) method and genetic algorithm could be considered as a substitution of the combination of the back propagation method and parameter increasing method, however, according to the considerations of the present inventors, in the case where an incredible large number of gene expression data are processed, the time is taken too much if this method in which the back propagation method is centered is employed. For example, in the case where the number of data is 6000 and over as in example, it would take about 30 hours to select one input and decide the parameters, and in the case where the number of parameters up to 5 inputs whose model is considered to be highly reliable, it would further take its 50-fold, that is, about 2 months, and it is impossible to use these for actual time processing. In contrast to this, according to a method in which the SWEEP operator method and the parameter increasing method are combined, it takes only less than 30 seconds to determine the parameters and the like under the conditions of utilizing the same computer hard resource.

The reason why the calculation time is made short is due to the characteristic of the SWEEP operator method in which ⅔ of parameters are fixed. In a FNN method, it is necessary to determine 6 pieces of parameters with respect to one input. In the SWEEP operator method, out of 6 pieces of parameters, 4 pieces (two pieces of Wc, Wg, respectively) are fixed, only two pieces (two pieces of Wf) maybe determined, and in BP method, in order that the most suitable parameters are derived, the same calculation must be repeated 1,000 times, but in the SWEEP operator method, it can be processed at one time, which are the reasons why the calculation time is short in the SWEEP operator method.

Moreover, as described later, according to a FNN model constructed by utilizing input variables selected by the method in which the SWEEP operator method and the parameter increasing method are combined, it has been capable of obtaining the diagnosis with a high precision.

As described above, the present invention has been carried out on the basis of the most suitable method that the present inventors have found and that has been constructed using a method in which the SWEEP operator method and the parameter increasing method are combined. Specifically, A method for processing expression data of genes, which comprises gene selection step of processing expression data of two or more genes using a method in which the SWEEP operator method and the parameter increasing method are combined and selecting genes to be processed, and the FNN model construction step of constructing a FNN model by making expression data of genes to be processed as input variables.

Hereinafter, the respective factors of the present invention will be described in detail.

Expression data of two or more genes represent, in general, the expression state of each gene in a DNA microarray. A method in which genes are selected by the SWEEP operator method and the parameter increasing method, and a model of FNN (Fuzzy Neural Network) on the relevant selected genes is constructed is effective in the case where a large number of 100 genes or more which are the objects of processing is subjected to the processing. It is because that in the case of a small number of genes to be processed, a reliable processing can be carried out even by the conventional method.

In the present invention, a method in which the SWEEP operator method and the parameter increasing method are combined is used as a method of selecting genes relating to the expression of phenomenon which is relating to the diagnosis out of a large number of genes. By combining this method and a FNN method described later, the reliability of genetic diagnosis might have been enhanced.

Now, the SWEEP operator method is one solution of a linear square regression analysis and as shown in FIG. 1, it can be considered that it is a regression equation without constant term.

In FIG. 1, as for Wc, considering a variety of data of respective data of input terms (x1, x2), it is defined that the average value or odds ratio is utilized. Wg is a constant, therefore, when gene expression data of a patient is used (inputted), the expression data is automatically converted into fuzzy number. For example, supposing that x1, small . . . 0.2,
x1, big . . . 0.8,
x2, small . . . 0.4, and
x2, big . . . 0.6, resulting in a1=0.6, b1=0.8, c1=1.2, and d1=1.4, and moreover, if the patient survives, for example, 4 years, it is defined to be y1=0.1.

In another patient, supposing that
x1, small . . . 0.5,
x1, big . . . 0.5,
x2, small . . . 0.8, and
x2, big . . . 0.2, in this case, resulting in a2=1.3, b2=0.7, c2=1.3, and d2=0.7, and moreover, if the patient die within 4 years, it is defined to be y1=0.9.

Here, these values are substituted into the equation and the solution is to be found. In the case of two inputs, if there are data of 4 patients, all of the solutions Wfa to Wfd are obtained. Since the number of the actual patients exceeds over 4 patients, the respective solutions Wfa to Wfd of the equation are to be found by method of least squares.

It should be noted that in the equation of FIG. 1, although coefficients Wc, Wg are capable of being determined by an optional method, it is preferable that these are determined on the basis of odds ratio or the average value of data distribution.

Next, all of the data is inputted using the respective solutions Wfa to Wfd which have been obtained and the outputted value and the actual data (y1=0.1, y1=0.9 or the like) are compared, and the difference (error) is found. The sequence of models which are in turn sequenced from the smallest error to the largest error is to be "sequencing of input terms using the SWEEP operator method".

BRIEF DESCRIPTION OF THE DRAWINGS

These and other objects and technical advantages of the present invention will be readily apparent from the following description of the preferred exemplary embodiments of the invention in conjunction with the accompanying drawings, in which:

FIG. 2 is a table indicating the sequencing of input terms using the SWEEP operator method, which is obtained by one input;

FIG. 3 is a table indicating the sequencing of input terms using the SWEEP operator method, which is obtained by two inputs;

FIG. 5 is a table indicating the diagnosis rule derived from the FNN model of Example 1 described in FIG. 4;

FIG. 6 is a table indicating the diagnosis rule derived from the FNN model of Example 2 described in FIG. 4;

FIG. 7 is a table indicating the diagnosis rule derived from the FNN model of Example 3 described in FIG. 4;

FIG. 8 shows the evaluation results by Kaplan-Meier plot.

FIG. 9 is a table indicating the sequencing of input terms using SWEEP operator method, which is obtained by one input in another Example;

FIG. 10 is a table indicating the sequencing of input terms using SWEEP operator method, which is obtained by two inputs;

FIG. 11 is a table indicating the sequencing of input terms using the SWEEP operator method, which is obtained by two inputs;

FIG. 14 is a table indicating the diagnosis rule derived from the FNN model of another Example;

FIG. 15 is a table indicating an example in which the actual output is applied to the diagnosis rule of FIG. 14.

DESCRIPTION OF THE PREFERRED EMBODIMENTS

In Examples, "sequencing of input terms using the SWEEP operator method" was performed as follows:

First, the gene expression data of patients with B-cell lymphoma (number of data: 58 (survivor after 4 years: 32, death: 26), number of genes: 6141) published on the Web were used as gene expression data which are to be objects of processing. In the relevant data, when supposing M represents the maximum expression amount and S represents the minimum expression amount among the patients, genes of M/S=3 or less, and M−S=100 or less have been excluded.

Now, the results that the above-described "sequencing of input items using the SWEEP operator method" was carried out by inputting only one gene expression data are shown in FIG. 2.

The point of the present invention is in that the results of FIG. 2 are further processed.

The parameter increasing method is a method concretely indicated as follows: a model is constructed using one gene selected from 6141 genes as candidate genes(In FIG. 1, corresponding to x1 input), and 6141 models of a model using one gene are constructed. Among these, a gene that has constructed the best model is fixed. One gene is in turn selected from the remaining 6140 pieces of genes (corresponding to x2 of FIG. 2), it is combined with the fixed gene (x1), 6140 models of a model using the two genes are constructed. Among these, two genes that have constructed the best models are, fixed. This operation is repeated.

Upper order 5 genes among genes sequenced in FIG. 2 are selected as first genes and a second gene for each of the first genes is chosen. The above-mentioned operations are repeated by using these two genes thus chosen. The results are shown in FIG. 3. Accordingly, "sequencing of input terms that the SWEEP operator method and the parameter increasing method are combined" is carried out.

In the respective tables of FIG. 3, the respective second genes are indicated at the uppermost level.

Here, it should be noted that the gene ranked at upper level in FIG. 2 is not necessarily ranked at upper level in the results of FIG. 3.

Therefore, in the present invention, the results of FIG. 3 were respected for, and the second gene and following 1–3 genes in the tables which made as smaller errors were selected. The genes to be processed are constituted of the second gene and the following 1–3 genes.

By making this gene to be processed as an input variable, and using parameters obtained on the relevant genes to be processed, a model of FNN has been constructed by utilizing the back propagation (BP) method.

Figure 1:
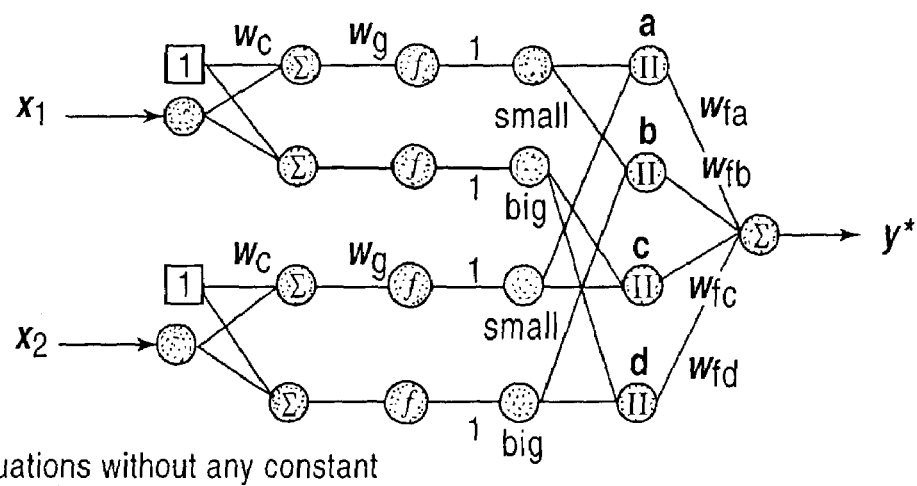
FIG. 1 is a conceptual diagram of the SWEEP operator method.

As a FNN method, a model having a structure shown in FIG. 1 (here, for simplification, the structure of the model of two-inputs one-output is shown) was used. The expression data of genes to be processed were used as input data, and survivor ratio after 4 years of the patients was used as an output. The gene expression data $X_i$ used for input were normalized with the maximum value M and the minimum value S of 58 patients of the respective genes as the following, and made it as normalization data $X_{i,norm}$.

$$X_{i,norm}=0.8\times(X_i-S)/(M-S)+0.1$$

The output-data were normalized as dead patient being 0.9 and surviving patient being 0.1, and these were also utilized as a tutor data of the model.

In order to construct a model, 58 pieces of data sets (gene expression data of the patients and data of surviving or death after 4 years) were divided into 4 groups of Group A consisted of 15 patients, Group B consisted of another 15 patients, Group C consisted of 14 patients and Group D consisted of the remaining 14 patients, and the results were evaluated by 4 ways of the combinations in a way where 14 patients of Group D were evaluated by making Group A, Group B and Group C as learning data, and 15 patients of Group A were evaluated by making Group B, Group C and Group D as learning data, and so on.

In the case where data of the dead patient was inputted, the tutor data (Ti) is 0.9. Therefore, if just 0.9 was outputted, the error is 0 and it was made as a correct solution but if the output was in the range from 0.6 to 1.2, it was made as a correct solution with the error, and in the case where it was the output except for these, it was made as an incorrect solution and was counted as outliers. As for the surviving patient, when the values in the range from −0.2 to 0.4 were outputted, it was made as a correct solution with the error.

The evaluation of a model was carried out by the ratio of outliers. In the case of a model using 44 sets of learning data, the number of outliers out of outputted data (Oi) was made as $N_L$, and the number of outliers of the data for evaluation was made as $N_E$. The ratio P of outliers was represented by the following equation, the learning of model was carried out so that this ratio became smaller.

$$P=N_L/N_{LT}+N_E/N_{ET}$$

where $N_{LT}$ and $N_{ET}$ are the total number of learning data and data for evaluation, for example, the number is 44 and 14, respectively.

If the ratio P of outliers became identical, it was evaluated by the average of the square error of the following equation, and the model in which the value becomes smaller was selected and learned.

The following evaluation criteriality J was used for evaluation of the FNN.

$$J=(J_1+J_2)/2$$

Where $J_1$ represents the average of the square error of learning data, and $J_2$ represents the average of the square error of data for evaluation, represented by the following equations:

$$J_1=(1/N_{LT})\Sigma(Oi-Ti)^2$$

$$J_2=(1/N_{ET})\Sigma(Oi-Ti)^2$$

The termination condition of learning of the FNN was made as the maximum learning number of times being 5,000 iteration.

The learning was carried out by dividing into two times as followings by the back propagation (BP) method. The initial weights (wg, wc and wf) were made as 0, the learning coefficient with respect to wf was made as 0.1, the learning coefficient with respect to wg and wc was made as 0, the learning was carried out up to the maximum learning number of times, that is, 5,000 iteration, and at the point where P becomes the minimum, the parameter wf was tentatively fixed. Next, the learning coefficient with respect to wc, wg and wf was made as 0.1, the learning was carried out up to the maximum learning number of times, and at the point where P becomes the minimum, the parameters wc, wg and wf were fixed. In the case where any one of these corresponds to each other, the weight at the time when the value of J became the minimum was selected.

Figure 4:
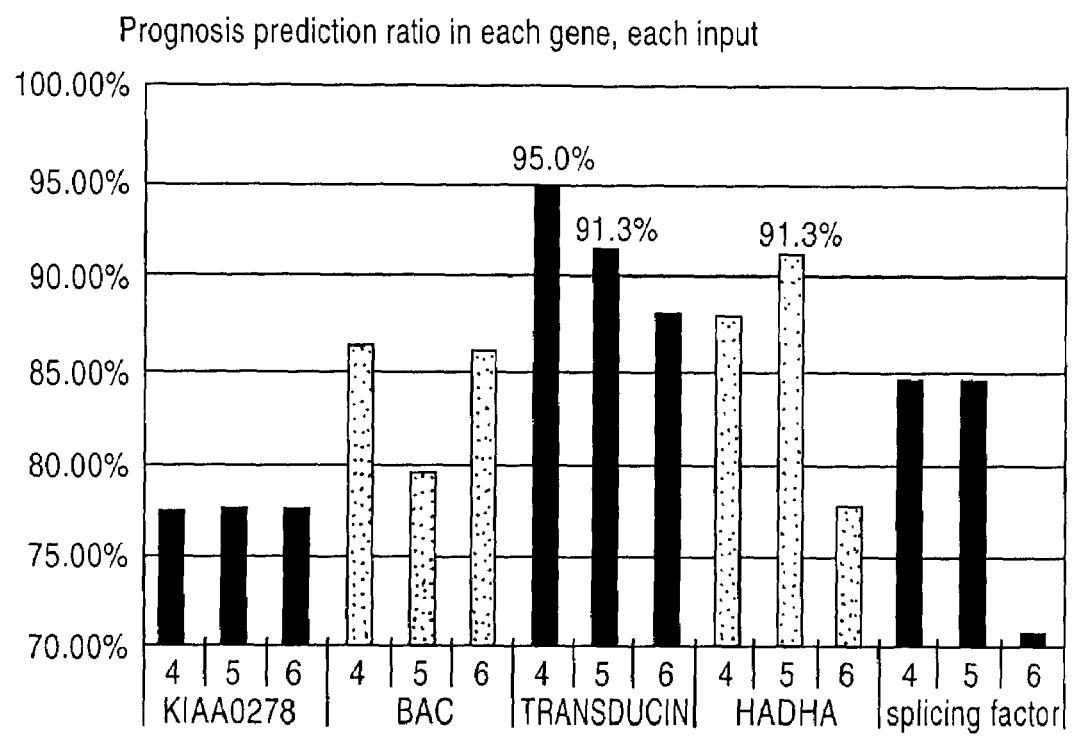
FIG. 4 is a graphical representation showing the precision of the results by the FNN model consisted of the selected genes.

The results that the expression data of the upper order genes of the results in FIG. 3 were inputted into the constructed model are shown in FIG. 4.

From the results of FIG. 4, the results that the prognosis prediction ratio is high is shown when the combination of the genes that TRANSDUCIN-LIKE ENHANCER PROTEIN 1 was made as fixed first gene was made genes to be processed. Particularly, the combination of 4 genes of TRANSDUCIN-LIKE ENHANCER PROTEIN 1, Oviductal glycoprotein mRNA, CDKN2A Cyclin-dependent kinase inhibitor 2A and Receptor tyrosine kinase DDR gene (Example 1) is preferable.

It should be noted that the combination of 5 genes of TRANSDUCIN-LIKE ENHANCER PROTEIN 1, Oviductal glycoprotein mRNA, CDKN2A Cyclin-dependent kinase inhibitor 2A, Receptor tyrosine kinase DDR gene and VIL2 Villin 2 (Example 2) is also preferable.

Moreover, the combination of 5 genes of HADAHA Hydroxyl-Coenzyme A dehydrogenase, Cytoplasmic antiproteinase 2(CAP2) mRNA, ADRB3 Adrenergic, beta-3-receptor, PRKACB gene and NF-AT3 mRNA (Example 3) is also preferable.

By the way, the prognosis prediction ratios at the time when 4, 5 and 6 pieces of genes ranked in FIG. 2 were selected from the upper level and FNN-processed similarly to the description described above were 69.1%, 75.8% and 70.6%, any of them did not reach 80%.

It is understood that from the results of FIG. 4, it is the most preferable that a model of FNN is constructed by making the combination of 4 genes of TRANSDUCIN-LIKE ENHANCER PROTEIN 1, Oviductal glycoprotein mRNA, CDKN2A Cyclin-dependent kinase inhibitor 2A and Receptor tyrosine kinase DDR gene as the genes to be processed.

In FIG. 5(A), the diagnosis rule derived by the FNN model constructed on Example 1 is indicated. For example, when TRANSDUCIN-LIKE ENHANCER PROTEIN 1 is small, Oviductal glycoprotein mRNA is small, CDKN2A Cyclin-dependent kinase inhibitor 2A is small and Receptor tyrosine kinase DDR gene is small, the weight in the consequences (Wfa in FIG. 1) is −3.02. Therefore, it is understood that in the case of the patient having such data, very small output value is outputted. It should be noted that the threshold value which assigns the expression data of the respective genes into the categories of being small and big has been adjusted by the learning of FNN.

The output results were obtained by substituting the expression data of above described 4 genes in the whole patients into a FNN model, the results grouped by referencing to the results of FIG. 5(A) are shown in FIG. 5(B). It should be noted that the individual of the patient is represented by the number, specifically, Nos. 1–32 are the surviving patients, and Nos. 33–58 are the dead patients.

From the results of FIG. 5(B), it is understood that when the expression data of TRANSDUCIN-LIKE ENHANCER PROTEIN 1 is small, the expression data of CDKN2A Cyclin-dependent kinase inhibitor 2A is big and the expression data of Receptor tyrosine kinase DDR gene is small, the prognosis is poor.

It should be noted that according to the considerations of the present inventor, in the results by the International Prognosis Index, these were determined as low risk on the prognosis of the patients of No. 38 and 49. Even in such a case, it is clear that if the diagnosis method of Example 1 is used, it is expected to be at a high risk, it is considered that the selection of therapeutic method may be also influenced.

In FIG. 6(A), the results of the diagnostic rule derived by the FNN model constructed on Example 2 are indicated. The output results were obtained by substituting the expression data of above-described 5 genes of Example 2 in the whole patients into the FNN model, the results grouped by referencing to the results of FIG. 6(A) are shown in FIG. 6(B). From the results of FIG. 6(B), it is understood that similar to Example 1, when the expression data of TRANSDUCIN-LIKE ENHANCER PROTEIN 1 is small, the expression data of CDKN2A Cyclin-dependent kinase inhibitor 2A is big and the expression data of Receptor tyrosine kinase DDR gene is small, the prognosis is poor.

It should be noted that the threshold when the gene expression is small or big in the example of FIG. 6 is not necessarily the same with that of FIG. 5. It is because the FNN models are different.

In FIG. 7(A), the results of the diagnostic rule derived by the FNN model constructed on Example 3 are indicated. The output results were obtained by substituting the expression data of 5 genes of Example 3 in the whole patients into the FNN model, the results grouped by referencing to the results of FIG. 7(A) are shown in FIG. 7(B). From the results of FIG. 7(B), it is understood that when the expression data of HADAHA Hydroxyl-Coenzyme A dehydrogenase is big, the expression data of Cytoplasmic antiproteinase 2 (CAP2) mRNA is small and the expression data of NF-AT3 mRNA is small, the prognosis is poor. It is also understood that when the expression data of ADRB3 Adrenergic, beta-3-receptor is big, the expression data of PRKACB gene is big, and the expression data of NF-AT3 mRNA is small, the prognosis is poor.

As described above, according to the prognostic diagnosis method for patients with B-cell lymphoma of Examples, the precision exceeding over 90% was capable of being achieved.

Figure 8A:
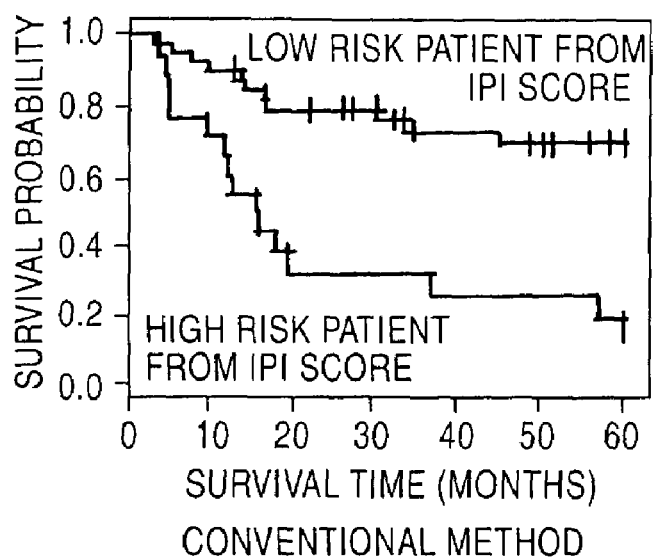
FIG. 8B is a plot on the evaluation results by the FNN model of Example 1 and FIG. 8A is a plot on the evaluation results by the conventional method of Example 1.
Figure 8B:
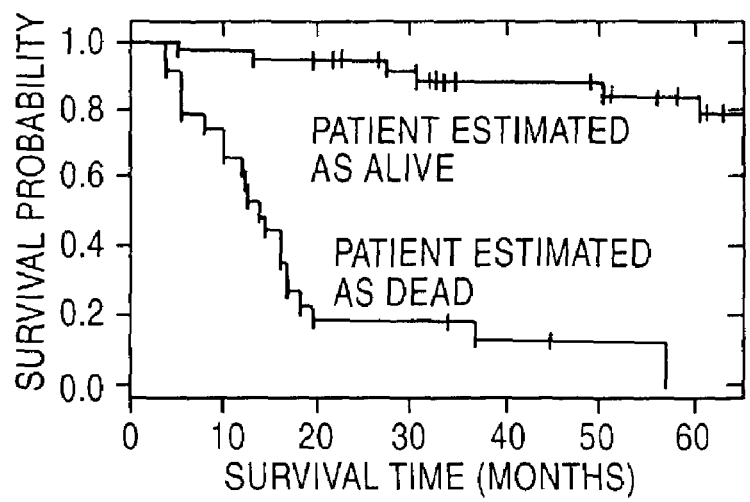

In FIG. 8B, the evaluation results by Kaplan-Meier Plot on Example 1 (FIG. 5) are shown. FIG. 8(A) shows the results using conventional method. Kaplan-Meier plot of the prognostic diagnosis described in the original literature (see Nature Medicine, Vol. 8, pp.68–74 (2002)) is shown.

From the results of FIG. 8, it is understood that according to the present invention, the prognostic diagnosis with an extremely high precision is capable of being realized.

Moreover, tables in FIG. 5–FIG. 7 show the evidences and reasons of the diagnosis. In this way, according to the FNN, a table which is to be the evidences of the diagnosis is capable of being derived in conjunction with, it is said that the FNN is an extremely suitable method. On the other hand, such an evidence is not capable of being derived by the NN (Neural Network) method.

It should be noted that the selection method of genes by the SWEEP operator method and the parameter increasing method employed in Example is a novel method, and particularly, the correctness of prognostic prediction from gene expression data in the combination with the FNN method is enhanced.

Moreover, it is also a novel method in which the selection of genes by the SWEEP operator method was combined with the FNN method.

It is also a novel method in which gene expression data is processed using the FNN method.

Next, Examples concerning with the gene expression data concerning with breast cancer will be described below.

As the gene expression data which are to be an object of the processing, data (see Original literature: Nature, 415, pp.530–536(2002)) published on the Web were used.

Now, the results of "Sequencing of input terms using the SWEEP operator method" by inputting only one gene expression data are shown in FIG. 9.

Next, "Sequencing of input terms using the SWEEP operator method" was carried out by fixing each of 10 genes of the upper order among genes sequenced as shown in FIG. 9 (in FIG. 1, corresponding to input of x1) and in turn selecting x2 from the other genes. The results are shown in FIG. 10 and FIG. 11.

A FNN model has been constructed similarly to examples of the already described lymphoma by making this gene to be processed as an input variable and by utilizing the obtained parameters on the relevant genes to be processed.

Figure 12:
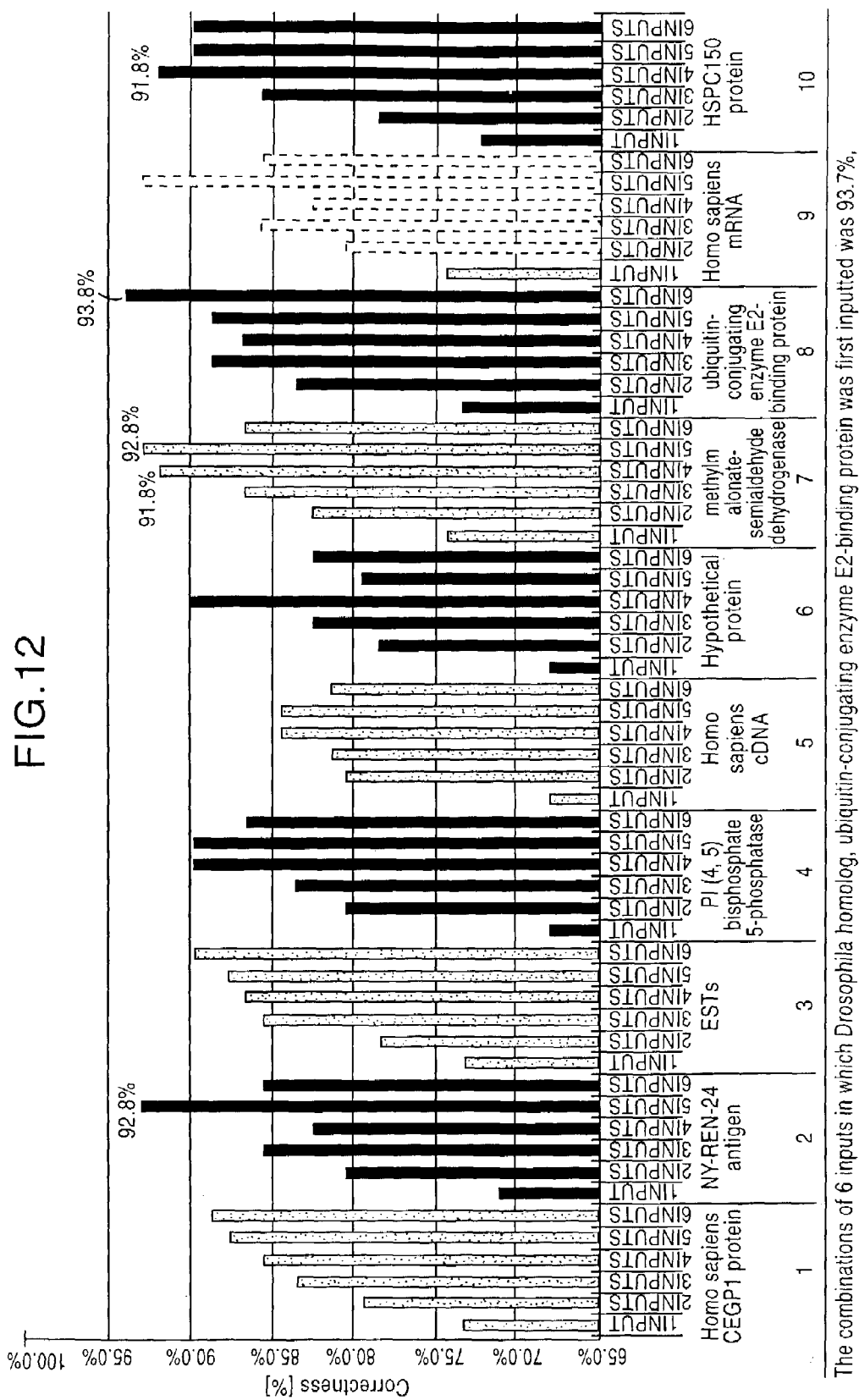
FIG. 12 is a graphical representation showing the precision of the results by the FNN models consisted of the selected genes.
Figure 13:
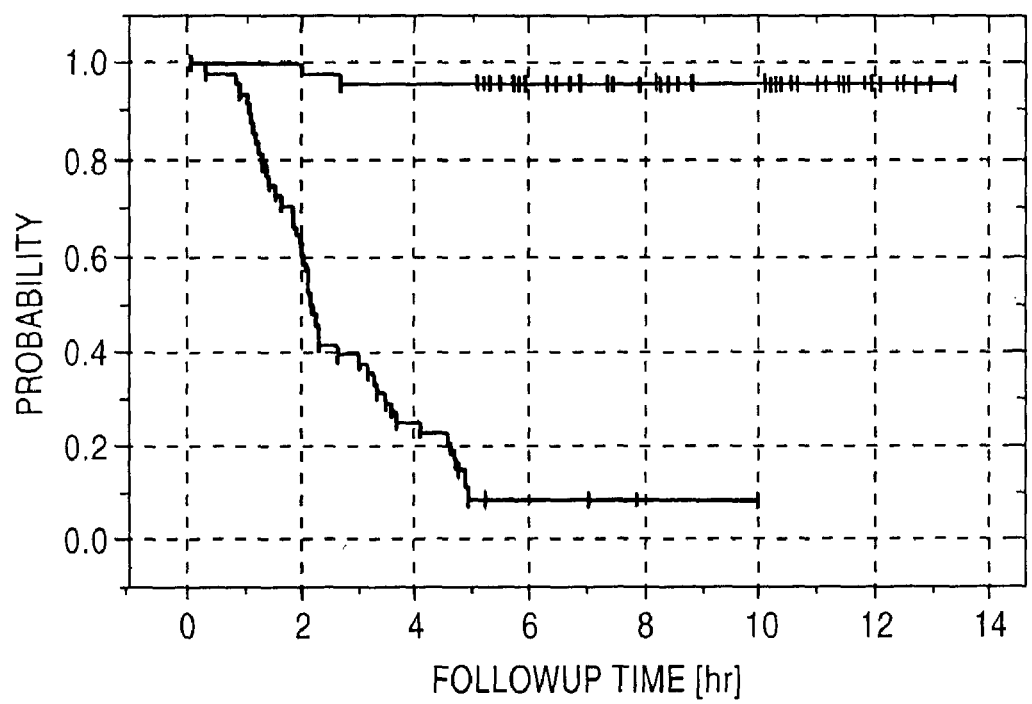
FIG. 13 shows the evaluation results by Kaplan-Meier plot.

The output results of the relevant FNN model are shown in FIG. 12. Moreover, Kaplan-Meier plot on No. 8 whose correctness is the highest is shown in FIG. 13. From the results of FIG. 12 and FIG. 13, it can be confirmed that according to the present invention, also in the prognostic diagnosis of breast cancer, a high precision is obtained.

It should be noted that in FIG. 14, the diagnostic rules derived by the FNN model constructed on the relevant No. 8 are shown. Moreover, in FIG. 15, the concrete results of diagnosis of the patients were applied to the diagnostic rule in FIG. 14.

In the above-described Example, although an example to which the present invention is applied to the prognostic diagnosis for patients with B-cell lymphoma and breast cancer has been indicated, the present invention is capable of applying to, needless to say, the prognostic diagnosis for the other diseases, and also applying to the prediction of occurrence of a variety of diseases by processing the expression data of a large amount of genes, the expression characteristic of side effects, the selection of a therapeutic drug or a therapeutic method or the like.

Furthermore, the present invention is also utilizable to the processing of mass data of a variety of the measured proteins. The results obtained by processing mass data of the proteins is capable of being applied to the prognostic diagnosis, the prediction of occurrence of a variety of diseases, the expression characteristic of side-effects, the selection of a therapeutic drug or a therapeutic method.

Figure 16:
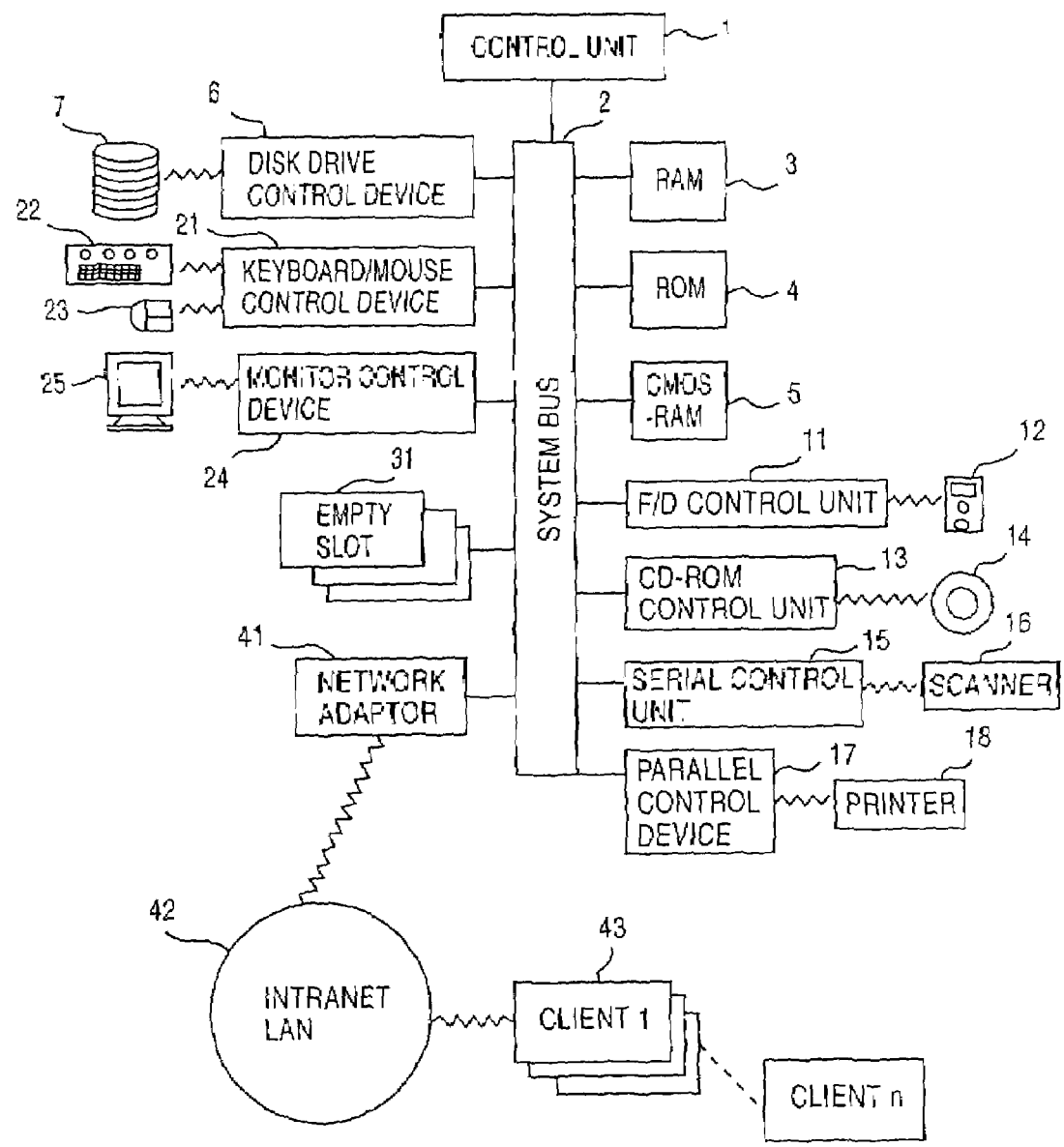
FIG. 16 shows a device of Example.

FIG. 16 is a block diagram showing a data processing system for carrying out the diagnostic method of the present Example. The configuration of this system is one in which a variety of factors are connected via a system bus 2 with respect to a central processing unit 1 similarly to the usual PC.

The central processing unit 1 comprises a general-purposed CPU, a memory control device, a bus control device, an intervening control device, and further a DMA (direct memory access) device, and further comprises a system bus 2, a data line, an address line and a control line. To the system bus 2, a memory circuit consisted of a RAM (random access memory) 3 and a nonvolatile memory (ROM 4, CMOS-RAM 5 or the like) is connected. The RAM 3 is read or rewritten by the central processing unit 1 and the other hardware factors. The data of the nonvolatile memory is exclusively used for read, data thereof is not deleted, even at the time when the unit is turned off. The system program for controlling this hardware is stored in a hard disk device 7, and also stored in the RAM 3, it is read via a disk drive control device 6 by the central processing unit 1 and used on the appropriate occasions. In this hard disk device 7, an application program for carrying out a variety of data processing is also stored. Moreover, data of the expression patterns are stored in the predetermined area of the hard disk device 7.

To the system bus 2, a floppy drive control device 11 which performs reading and wiring of data with respect to a floppy disk 12 and a CD-ROM control device 13 which performs the reading of the data from a compact disk 14 are connected. In the present Example, a scanner (DNA scanning device) 16 is connected to a serial control device 15, and a printer 18 is connected to a parallel control device 17. These control devices 15 and 17 make the connections of two or more factors possible, and optical factors are capable of being connected to these.

To the system bus 2, a keyboard/mouse control device 21 is connected, thereby making data input from a keyboard 22 and a mouse 23 possible. A monitor 25 is connected via a monitor control device 24 to the system bus 2. For the monitor 25, a CRT type, a liquid crystal type, a plasma display type or the like is capable of being utilized.

An empty slot 31 is prepared for the purpose of making the extension of a variety of factors (modem and the like) possible.

The system of Examples is connected to a network 42 via a network adaptor 41. The other system which is to be a client 43 has been connected to this network (intranet) 42. The system configuration of each client 43 is also substantially the same with that of FIG. 9. Moreover, this network 42 is connected to via a fire wall to the exterior internet.

Programs (OS program, application program (including the programs of the present invention)) necessary for making the system of Examples are installed via a variety of media. It is possible to install it for example, in a non-write record medium (CD-ROM, ROM card or the like), in a writable record medium (FD, DVD or the like), and further in a form of a communication medium by utilizing the network 42. Needless to say, it is capable of being done that these programs have been previously written in the non-volatile memories 4, 5 and the hard disk device 7.

In the description described above, the program for carrying out the SWEEP operator method, the parameter increasing method or the like, or the FNN modeling is stored in the hard disk 7. The expression data of the respective genes are stored in a form of table in the hard disk 7.

The programs for carrying out the diagnostic method of Examples are capable of being stored in a record medium such as a CD-ROM or the like. Moreover, it is also capable of being transferred to the other computer device via the internet or the like.

The present invention is not limited to the description of Embodiments and Examples of the above-described invention at all. The present invention also includes a variety of modified Embodiments in the scope that those skilled in the art is capable of easily conceiving without departing from the description within the scope of the claims.

We claim:

1. A method for processing expression data of genes, said method comprising:
   a gene selection step of processing expression data of specimen genes using a SWEEP operator method and a parameter increasing method and selecting genes to be processed, and
   a FNN model constructing step of constructing a FNN model by making expression data of said genes to be processed as input variables.

2. The method for processing expression data of genes as claimed in claim 1, wherein in said gene selection step, each expression data of said specimen genes is processed using said SWEEP operator method as one input data and a predetermined number of first genes are selected,
   choosing a second gene in said first genes, said second gene and at least one of the remaining genes in said specimen genes are combined, these expression data are processed by said SWEEP operator method to select third or more genes in said remaining genes, and said genes to be processed are constituted with said second gene and said third or more genes.

3. A method for diagnosing diseases, said method comprising:

a gene selection step of processing expression data of specimen genes using a SWEEP operator method and a parameter increasing method and selecting genes to be processed, and a FNN model constructing step of constructing a FNN model by making expression data of said genes to be processed as input variables, wherein diagnosis is performed based on said genes to be processed using said constructed FNN model.

4. The method for diagnosing diseases as claimed in claim 3, wherein said genes to be processed are TRANSDUCIN-LIKE ENHANCER PROTEIN 1, oviductal glycoprotein mRNA, CDKN2A Cyclin-dependent kinase inhibitor 2A and Receptor tyrosine kinase DDR gene, and an object of diagnosis is prognostic diagnosis for a patient with lymphoma.

5. A method for selecting genes, wherein expression data of specimen genes are processed by a SWEEP operator method and genes to be processed are selected.

6. The method for selecting genes as claimed in claim 5, wherein a predetermined number of first genes are selected, choosing a second gene in said first genes, said second gene and at least one of the remaining genes in said specimen genes are combined, these expression data are processed by said SWEEP operator method to select third or more genes in said remaining genes, and said genes to be processed are constituted with said second gene and said third or more genes.

7. A method for processing expression data of genes, said method comprising:

a gene selection step of processing expression data of specimen genes using a SWEEP operator method and selecting genes to be processed, and a FNN model constructing step of constructing a FNN model by making expression data of said genes to be processed as input variables.

8. A method for processing expression data of genes, wherein a predetermined number of genes are processed using a FNN model.

9. A program for processing expression data of specimen genes, said program for making a computer execute a gene selection step of processing expression data of specimen genes using a SWEEP operator method and a parameter increasing method and selecting genes to be processed, and a FNN model constructing step of constructing a FNN model by making expression data of said genes to be processed as input variables.

10. The computer program as claimed in claim 9, wherein in said gene selection step, each expression data of said specimen genes is processed using said SWEEP operator method as one input data and a predetermined number of first genes are selected, choosing a second gene in said first genes, said second gene and at least one of the remaining genes in said specimen genes are combined, these expression data are processed by said SWEEP operator method to select third or more genes in said remaining genes.

11. A computer program, wherein diagnosis is performed based on said genes to be processed using said constructed FNN model set forth in claim 1.

* * * * *